United States Patent
Sharifian et al.

[11] Patent Number: 6,024,855
[45] Date of Patent: Feb. 15, 2000

[54] ELECTROSYNTHESIS OF HYDROXYLAMMONIUM SALTS AND HYDROXYLAMINE USING A MEDIATOR

[75] Inventors: Hossein Sharifian, Austin, Tex.; John H. Wagonknecht, Cedar Hill, Mo.

[73] Assignee: Sachem, Inc., Austin, Tex.

[21] Appl. No.: 09/133,851

[22] Filed: Aug. 13, 1998

Related U.S. Application Data

[60] Provisional application No. 60/055,823, Aug. 15, 1997.

[51] Int. Cl.$^7$ ..................................................... B01D 61/44
[52] U.S. Cl. .......................... 204/522; 205/431; 204/535; 204/537
[58] Field of Search ................................... 205/431, 435, 205/436; 204/522, 535, 537

[56] References Cited

U.S. PATENT DOCUMENTS

| | | | |
|---|---|---|---|
| 2,719,778 | 10/1955 | Jockers et al. | 23/190 |
| 4,321,313 | 3/1982 | Langer et al. | 429/13 |
| 4,645,579 | 2/1987 | Weiss et al. | 204/182.4 |
| 4,818,353 | 4/1989 | Langer et al. | 204/74 |
| 4,849,073 | 7/1989 | Dotson et al. | 204/101 |
| 4,968,394 | 11/1990 | Dotson et al. | 204/101 |
| 5,281,311 | 1/1994 | Sharifian et al. | 204/101 |
| 5,447,610 | 9/1995 | Sharifian | 204/101 |

FOREIGN PATENT DOCUMENTS

| | | |
|---|---|---|
| 0106197A | 4/1984 | European Pat. Off. . |
| 0225659A | 6/1987 | European Pat. Off. . |
| 2028157A | 10/1970 | France . |
| 2602802 | 2/1988 | France . |
| 4428255A1 | 8/1994 | Germany . |
| 44228255A | 2/1996 | Germany . |
| 04021507 | 1/1992 | Japan . |
| 1245786A | 9/1971 | United Kingdom . |
| 1400758A | 7/1975 | United Kingdom . |
| 1515190A | 6/1978 | United Kingdom . |

OTHER PUBLICATIONS

Chih–Hsing Yu et al.; "Electrocatalytic Reduction Of Nitric Oxide by Water–Soluble Manganese Porphyrins"; Chemical Abstracts, vol. 121, No. 6 (Aug. 8, 1994).

(List continued on next page.)

Primary Examiner—Arun S. Phasge
Attorney, Agent, or Firm—Renner, Otto, Boisselle & Sklar, P.L.L.

[57] ABSTRACT

In one embodiment, the present invention relates to a method of preparing a hydroxylammonium salt, involving the steps of: providing an electrochemical cell containing an anode, a cathode, and a divider positioned between the anode and the cathode, to define a catholyte compartment between the cathode and the divider and an anolyte compartment between the anode and the divider; charging the catholyte compartment with a first solution comprising a nitrogen containing compound and a mediator and the anolyte compartment with a second solution comprising an ionic compound; passing a current through the electrochemical cell to produce a hydroxylammonium salt in the catholyte compartment; and recovering the hydroxylammonium salt from the catholyte compartment. In another embodiment, the present invention relates to a method of preparing hydroxylamine, involving the steps of: providing an electrochemical cell containing an anode, a cathode and a divider positioned between the cathode and the anode, to define a catholyte compartment between the cathode and the divider, and an anolyte compartment between the divider and the anode; charging the catholyte compartment with a solution comprising a hydroxylammonium salt and a mediator, and the anolyte compartment with a first electrolyte solution; passing a current through the electrochemical cell to produce hydroxylamine in the catholyte compartment; and recovering hydroxylamine from the catholyte compartment.

29 Claims, 3 Drawing Sheets

OTHER PUBLICATIONS

Lisitsyn Yu et al.; "Role Of The Mediator System Ti(IV)/Ti(III) In The Electrosynthesis Of Aromatic Amines On A Copper Cathode", Chemical Abstracts, vol. 126, No. 2 (Jan. 13, 1997).

Isao Taniguchi et al.; "Electrocatalytic Reduction Of nitrate And Nitrite To Hydroxylamine And Ammonia Using Metal Cyclams"; Chemical Abstracts, vol. 107, No. 6 (Aug. 10, 1987).

Colucci et al., "The Electro Reduction Of Nitric Oxide On Bulk Platinum In Acid Solutions", Electrochimica Acta, vol. 30, No. 4 (1985), pp. 521–528.

Bathia et al., "Hydroxylamine Production By Electroreduction Of Nitric Oxide In A Trickle Bed Cell", The Canadian Journal of Chemical Engineering, vol. 57, No. 5 (Oct. 1979), pp. 631–637.

ELECTROSYNTHESIS OF HYDROXYLAMMONIUM SALTS AND HYDROXYLAMINE USING A MEDIATOR

This application claims benefit of Provisional Application 60/005,823 filed Aug. 15, 1997.

TECHNICAL FIELD

The present invention relates to methods for preparing hydroxylammonium salts and hydroxylamine using a mediator. More particularly, the invention relates to methods involving the use of a mediator or a film formed by the mediator for electrochemically converting a nitrogen containing compound to a hydroxylammonium salt, and then converting the hydroxylammonium salt to hydroxylamine.

BACKGROUND OF THE INVENTION

Hydroxylammonium salts may be represented by the formula:

$$(NR_2HOH)^+{}_yX^{-y}$$

wherein each R is hydrogen or a hydrocarbon group containing from 1 to about 8 carbon atoms, X is an anion of an acid and y is a number equal to the valence of X. Hydroxylammonium salts are compounds which have a variety of applications. For instance, hydroxylammonium nitrate may be used as a component of liquid propellant and as a reducing agent in photographic graphic operations. In some of these applications, it is desirable that a hydroxylammonium salt solution of high purity is available.

There exist several production methods to manufacture hydroxylammonium salts. In the case of hydroxylammonium nitrate for example, some of these methods include: electrodialysis of hydroxylammonium chloride and nitrate; reaction of hydroxylammonium sulfate and barium nitrate; three-step cation exchange process employing hydroxylammonium sulfate and nitric acid; and electrolytic reduction of nitric acid. Some of these methods, however, do not provide hydroxylammonium salt solutions of high purity which some applications of the compound require. As a result, procedures have been developed to purify the hydroxylammonium salt solutions produced by existing methods. Nevertheless, there remains a substantial demand for large quantities of high purity hydroxylammonium salt solutions.

Hydroxylamine is useful as an intermediary in chemical processes especially in the pharmaceutical and agricultural industries. It is also useful in stripper formulations. Stripper formulations may be used to remove photoresists from or clean a substrate. For example, hydroxylamine stripper solutions are used to remove polyamide coatings from metal foil. Hydroxylamine stripper solutions are utilized in the printed circuit board and semiconductor industries.

Frequently, solutions of hydroxylamine, especially solutions prepared from hydroxylammonium salts, contain undesirable amounts of impurities such as salts, ammonium ions, metals and organic materials. Thus, there also exists a need for hydroxylamine solutions having high purity.

French Patent 2,602,802 is directed to an electrolytic process to directly produce high purity solutions of hydroxylammonium nitrate from nitric acid. In particular, a process is described for producing by electrolysis a hydroxylammonium nitrate solution in an electrochemical cell containing a cathode compartment, an anode compartment and a separator between the cathode compartment and anode compartment. The process is characterized in that it includes the following operations: (a) introducing a catholyte, essentially containing an aqueous nitric acid solution, in the cathode compartment; (b) introducing an anolyte solution into the anode compartment; (c) electrolyzing the catholyte to a cathode potential between about 0.5 and 1.4 volts compared to the standard calomel electrode, while keeping the temperature of the reaction to the cathode below about 50° C., in order to produce a hydroxylamine solution; and (d) recovering the hydroxylammonium nitrate solution from the cathode compartment.

U.S. Pat. No. 4,645,579 relates to aqueous solutions of hydroxylamine which are prepared from aqueous hydroxylammonium salt solutions by electrodialysis by a method in which the aqueous hydroxylammonium salt solution is fed into the middle zone of an electrolysis cell, which is divided into a cathode zone, an anode zone and a middle zone by means of semipermeable membranes, and is electrolyzed, and the catholyte used is an alkali metal hydroxide solution containing ammonia and/or amines.

The production of hydroxylamine by the electroreduction of nitric oxide in sulfuric acid is described by L. J. J. Janssen et al in *Electrochimica Acta,* 1977, Vol. 22, pp. 27–30 and by M. L. Bathia et al in *The Canadian Journal of Chemical Engineering,* Vol. 57, October 1979, pp. 631–7. Janssen et al utilize a platinum cathode, and Bathia et al utilize a cathode bed of tungsten carbide particles. The electroreduction of nitric oxide on bulk platinum in perchloric acid and sulfuric acid solutions is described by J. A. Colucci et al in *Electrochimica Acta,* Vol. 30, No. 4, pp. 521–528, 1985.

U.S. Pat. No. 5,281,311 relates to a process in an electrolysis cell involving (A) providing an electrolysis cell containing an anolyte compartment containing an anode, a catholyte compartment containing an oxygen-consuming cathode and an anionic divider separating the anolyte and catholyte compartments; (B) providing an aqueous solution containing an acid and water to the anolyte compartment, and an aqueous solution containing hydroxylamine salt, water and optionally, an acid to the catholyte compartment; (C) charging an oxygen-containing gas to the catholyte compartment; (D) passing a direct current through the electrolysis cell for a period of time effective to reduce the acid content in the catholyte compartment and/or to convert the salt to a hydroxylamine; and (E) recovering a hydroxylamine or a hydroxylamine salt solution containing a reduced amount of acid from the catholyte compartment.

U.S. Pat. No. 5,447,610 relates to preparing hydroxylamine and hydroxylammonium salts by electrolytically reducing a mixture containing at least one nitrogen oxide and either a neutral electrolyte to form hydroxylamine or an acidic electrolyte such as an organic or inorganic acid to form a hydroxylammonium salt. The electrolytic reduction is conducted in an electrolysis cell containing an anolyte compartment containing an anode, a catholyte compartment containing a cathode, and a divider separating the anolyte and catholyte compartments where the mixture of at least one nitrogen oxide and the electrolyte is present in the catholyte compartment, and an acid is present in the anolyte compartment.

SUMMARY OF THE INVENTION

In one embodiment, the present invention relates to a method of preparing a hydroxylammonium salt, involving the steps of: providing an electrochemical cell containing an anode, a cathode, and a divider positioned between the anode and the cathode, to define a catholyte compartment between the cathode and the divider and an anolyte compartment between the anode and the divider; charging the catholyte compartment with a first solution comprising a nitrogen containing compound and a mediator and the anolyte compartment with a second solution comprising an ionic compound; passing a current through the electrochemical cell to produce a hydroxylammonium salt in the catholyte compartment; and recovering the hydroxylammonium salt from the catholyte compartment.

In another embodiment, the present invention relates to a method of making a hydroxylammonium salt by reducing a nitrogen containing compound, where a mediator is used with the nitrogen containing compound.

In yet another embodiment, the present invention relates to a method of preparing hydroxylamine, involving the steps of: providing an electrochemical cell containing an anode, a cathode, and a divider positioned between the cathode and the anode, to define a catholyte compartment between the cathode and the divider and an anolyte compartment between the divider and the anode; charging the catholyte compartment with a solution comprising a hydroxylammonium salt and a mediator, and the anolyte compartment with a first electrolyte solution; passing a current through the electrochemical cell to produce hydroxylamine in the catholyte compartment; and recovering hydroxylamine from the catholyte compartment.

In still yet another embodiment, the present invention relates to a method of making hydroxylamine from a hydroxylammonium salt in an electrochemical cell, where a mediator is used with the hydroxylammonium salt.

In another embodiment, the present invention relates to a method of preparing a hydroxylammonium salt, involving the steps of: providing an electrochemical cell containing an anode, a cathode, and a divider positioned between the anode and the cathode, to define a catholyte compartment between the cathode and the divider and an anolyte compartment between the anode and the divider, wherein the cathode has a film thereon formed from a mediator; charging the catholyte compartment with a first solution comprising a nitrogen containing compound and the anolyte compartment with a second solution comprising an ionic compound; passing a current through the electrochemical cell to produce a hydroxylammonium salt in the catholyte compartment; and recovering the hydroxylammonium salt from the catholyte compartment.

The present invention provides inexpensive and uncomplicated electrochemical methods of preparing hydroxylammonium salts and hydroxylamine of high purity.

DESCRIPTION OF THE PREFERRED EMBODIMENT

Figure 1:
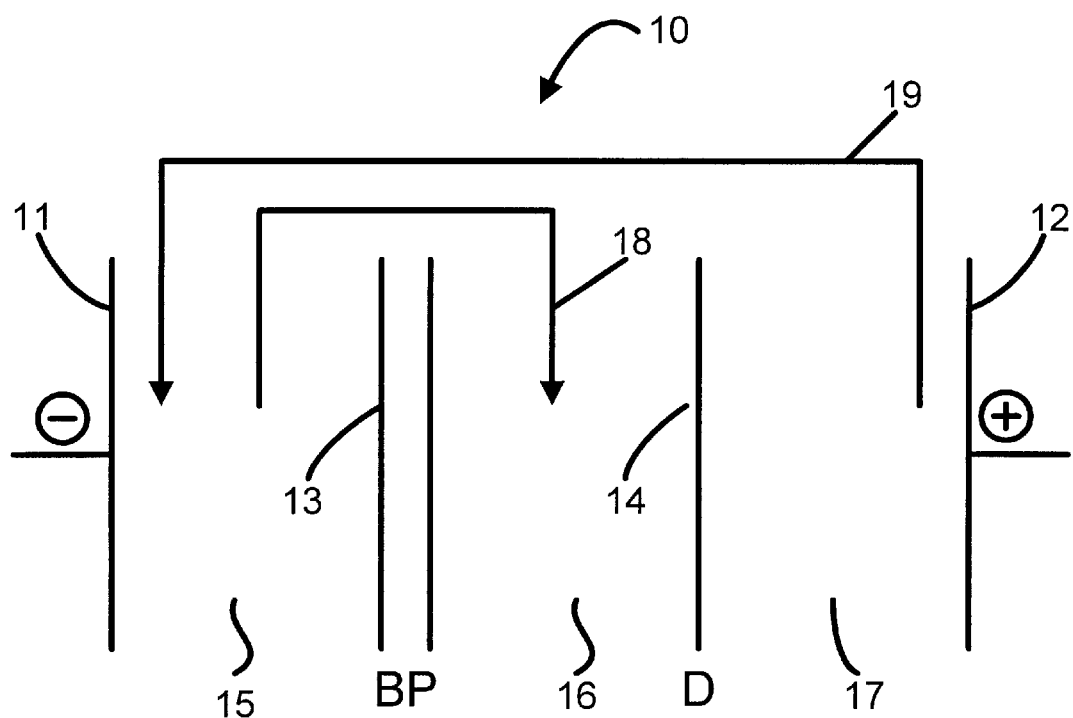
FIG. 1 is a schematic cross-section of an electrochemical cell useful in preparing hydroxylammonium salts and hydroxylamine according to the invention.

In one embodiment of the invention, the methods of preparing hydroxylammonium salts and hydroxylamine involve electrochemically converting a nitrogen containing compound in the presence of a mediator or a film formed by the mediator to initially form a hydroxylammonium salt. The nitrogen containing compound is reduced to a hydroxylammonium salt in the presence of a mediator or a film formed by the mediator. The hydroxylammonium salt is then electrochemically converted to hydroxylamine.

Nitrogen containing compounds are compounds containing at least one atom of nitrogen and which are capable of being converted to a hydroxylammonium salt in accordance with the present invention. Examples of nitrogen containing compounds include nitric acid, alkali metal nitrates such as sodium nitrate and potassium nitrate, alkaline earth metal nitrates such as magnesium nitrate and calcium nitrate, alkali nitrites such as sodium nitrite and potassium nitrite, alkaline earth metal nitrites, nitrides such as calcium nitride and magnesium nitride, organo-nitro compounds such as nitromethane, nitroethane, nitropropane, nitrobutane, nitrobenzene, etc., and nitrogen containing gases.

A nitrogen containing gas as used herein includes any gas containing an atom of nitrogen. Examples of nitrogen containing gas include nitrogen oxide gas and nitrogen-hydrogen gas. Nitrogen oxide gas as used herein is intended to mean a gas containing nitrogen and oxygen atoms. Examples of nitrogen oxide gas include one or more of nitric oxide (NO), nitrogen dioxide ($NO_2$), nitrogen trioxide ($NO_3$), dinitrogen trioxide ($N_2O_3$), dinitrogen pentoxide $NO_2O_5$. Nitrogen-hydrogen gas includes ammonia, hydrazine, and derivatives thereof. Nitrogen containing gas may also be any gas containing at least a nitrogen containing gas, for instance, a mixture of one or more inert gases and nitrogen oxide gas. Inert gases include nitrogen and the noble gases. The noble gases include helium, neon, argon, krypton, xenon and radon.

A mediator is a compound which promotes the conversion of a nitrogen containing compound to a hydroxylammonium salt. The mechanism for this conversion is not completely understood. One having ordinary skill in the art can determine whether or not a prospective mediator will indeed function as a mediator as defined herein by assembling the electrochemical cell of FIG. 1 or 2 and practicing the inventive method (for example, the method of the description of the operation of the electrochemical cell of FIG. 1 or 2) using the prospective mediator as the mediator or a film formed by the prospective mediator. The prospective mediator may be classified as a mediator if it or a film formed thereby promotes the conversion of a nitrogen containing compound to a hydroxylammonium salt. Preferably, the prospective mediator may be classified as a mediator if it or a film formed thereby promotes the conversion of a nitrogen containing compound to a hydroxylammonium salt at a rate faster than the conversion in the same electrochemical cell under the same conditions except that the prospective mediator is not used.

Although not wishing to be bound by any particular theory, it is believed that at least one of the three following functions is attributable to the mediator. First, a mediator may be a reducible compound capable of transferring electrons to a nitrogen containing compound thereby promoting its conversion to a hydroxylammonium salt. In this instance, the mediator has an oxidized and reduced state and/or is capable of donating, accepting or otherwise transferring electrons. During the process of the present invention, it is believed that the following electrochemical and chemical reactions may take place.

$$M^{(n+x)+}+xe^-\leftrightarrows M^{n+} \qquad \text{(I)}$$

$$M^{n+} + NCC \rightarrow M^{(n+x)+} + HAS \quad (II)$$

In the above equations, M is a mediator, n is the valence of the mediator in reduced form, x is the number of electrons the mediator can transfer when in its oxidized form, NCC is a nitrogen containing compound, and HAS is a hydroxylammonium salt. The mediator in reduced form ($M^{n+}$) can be regenerated from the mediator in oxidized form ($M^{(n+x)+}$) at the cathode of an electrochemical cell in which it is used. Second, a mediator may alter the surface of the electrode (such as the cathode) in such a way so as to promote the production of a hydroxylammonium salt. In this instance, the interaction between the mediator and an acid and/or nitrate ions may form a film covering the electrode (such as the cathode). Third, a mediator, by forming a film on an electrode, may increase the over-potential of hydrogen evolution at the electrode (such as the cathode) thereby promoting the production of a hydroxylammonium salt.

The chemical identity of the film formed on the electrode due to the presence of a mediator is unknown. However, the film forms substantially uniformly and smoothly over the electrode. The film typically is dark orange to brown in color. The film is typically solid versus porous. The film strongly adheres to the electrode. The film has an apparent catalytic effect of promoting the conversion of a nitrogen containing compound to a hydroxylammonium salt and/or promoting the conversion of a hydroxylammonium salt to hydroxylamine.

The thickness of the film depends upon the length of time that the process is conducted in the presence of a mediator. The film typically has a thickness from about 0.1 nm to about 500 $\mu$m. In another embodiment, the film has a thickness from about 0.5 nm to about 100 $\mu$m. In another embodiment, the film has a thickness from about 1 nm to about 10 $\mu$m.

The film forms fairly rapidly during the first hour of operation, and may last (retain apparent catalytic effect) for at least 3 months. In this connection, once an electrode (such as a cathode) has such a film formed thereon, it is not necessary to include a mediator in the solution charged to the electrochemical cell. In other words, when an electrochemical cell containing an electrode with such a film thereon is emptied, the solution recharged to cell need only contain a nitrogen containing compound and preferably an acid (without a mediator) in order to produce a hydroxylammonium salt by electroreduction.

Mediators include organic mediators and inorganic mediators. Inorganic mediators include metal mediators and non-organic mediators capable of being reversibly reduced and oxidized. For instance, inorganic mediators include metals (represented as Me) having an oxidized and reduced form, such as $Me^{(n+x)+}$ and $Me^{n+}$, respectively. Inorganic mediators include at least one of a cesium compound, a chromium compound, a cobalt compound, a copper compound, a manganese compound, a periodate compound, a silver compound, a sodium compound, a tin compound, a titanium compound, and a zinc compound. Specific examples of inorganic mediators include $Ag^{2+}/Ag^+$, $Ce^{4+}/Ce^{3+}$, $Co^{3+}/Co^{2+}$, $Cr^{3+}/Cr^{2+}$, $Cu^{2+}/Cu^+$, $Mn^{3+}/Mn^{2+}$, $Sn^{2+}/Sn^{4+}$, $Ti^{3+}/Ti^{4+}$, $Zn^{2+}/Zn^0$, $IO_4^-/IO_3^-$, and $Na^+/Na(Hg)$. Inorganic mediators can be added to an electrochemical cell in metal form (adding metal powder) or in salt form. Salts of the metals mentioned above are known, such as acetate, bromide, carbonate, chloride, fluoride, iodide, nitrate, oxalate, phosphate and sulfate salts (see also the various anions of the hydroxylammonium salts described below), and thus a long list is not included here.

Organic mediators include aromatic compounds and heterocyclic compounds capable of donating and accepting electrons or transferring electrons. Preferred organic mediators include amino-aromatic compounds and quinone compounds. Specific examples of organic mediators include 1,4-phenylenediamine; 1,3-phenylenediamine; tetracyanoquinodimethane; N,N,N',N'-tetramethyl-p-phenylenediamine; aminophenols such as p-aminophenol, m-aminophenol and o-aminophenol; aminothiophenols; tetrathiafulvalene; thianthrene; tri-N-p-tolyamine; ferrocene; methylviologen dichloride hydrate; quinone compounds such as hydroquinone, aminoanthraquinones, aminoanthraquinone-2-sulfonic acid sodium salt, anthraquinone-1,5-disulfonic acid disodium salt, and anthraquinone-2,6-disulfonic acid disodium salt; aniline compounds such as acetanilide, 4-bromo-2,3,5,6-tetrafluoroaniline, 4,4'-oxydianiline, and 4'-aminoacetanilide; 1,10-phenanthroline; phenazine; 1,8-diaminonaphthalene; 1,4-diacetylbenzene; terephthaldicarboxaldehyde; terephthalic acid; and 2,5-dichloro-1,4-phenylenediamine.

The solutions used in the electrochemical cells may contain an ionic compound, such as an electrolyte. Ionic compounds used in the invention are chemical compounds that partially or fully ionize in solution. Examples of ionic compounds include salts, metal salts, bases and acids or any compound which forms an anion and/or cation when dissolved in solution. The electrochemical cells may contain one or more ionic compounds.

The term "solution" herein means aqueous and nonaqueous solutions operable in the invention. Thus, a solution may contain one or more of water, protic solvents, organic solvents such alcohols and the like. The water used in any of the solutions of the present invention is preferably deionized water, and more preferably very pure deionized water.

In one embodiment, the ionic compound is an acid and a solution of the acid is an acidic electrolyte. An acid lowers the pH of a neutral solution. Acids include organic and inorganic acids. Preferably, the acid is not reactive at the cathode.

Specific examples of inorganic acids represented by formula $H_yX$ which may be utilized in the acidic electrolyte with the nitrogen containing compound include at least one of nitric acid, halogen acids such as hydrofluoric acid, hydrochloric acid, hydrobromic acid and hydriodic acid, sulfuric acid, sulfurous acid, perchloric acid, boric acid and phosphorus acids such as phosphorous acid and phosphoric acid. Nitric acid and sulfuric acid are preferred inorganic acids. Nitric acid and any other acid are preferred combinations of acids. Examples of organic acids represented by the formula $H_yX$ include carboxylic and polycarboxylic acids such as formic acid, acetic acid, propionic acid, citric acid, oxalic acid, etc.; organic phosphorus acids such as dimethylphosphoric acid and dimethylphosphinic acid; or sulfonic acids such as methanesulfonic acid, ethanesulfonic acid, 1-pentanesulfonic acid, 1-hexanesulfonic acid, 1-heptanesulfonic acid, benzenesulfonic acid, toluenesulfonic acid, etc. Nitric acid and any other acid are preferred combinations of acids.

In one embodiment, the ionic compound is a base and a solution of the base is a basic electrolyte. A base increases the pH of a neutral solution. Bases include organic and inorganic bases.

Bases include alkali metal and alkaline earth metal hydroxides, silicates, phosphates, borates, carbonates, and mixtures thereof. For example, the basic compound includes alkali metal hydroxides, alkaline earth metal hydroxides, alkali metal silicates and so on. Alkali metals include lithium, sodium, potassium, rubidium and cesium. Alkaline earth metals include beryllium, magnesium, calcium, strontium, and barium. Specific bases include sodium tetraborate, sodium carbonate, sodium bicarbonate, sodium hydroxide, sodium phosphate, sodium pyrophosphate and other polyphosphates, sodium silicate, potassium carbonate, potassium bicarbonate, potassium hydroxide, potassium phosphate, potassium pyrophosphate and other polyphosphates, calcium carbonate, calcium hydroxide, calcium phosphate, calcium pyrophosphate, calcium silicate, magnesium carbonate, magnesium hydroxide, magnesium phosphate, magnesium pyrophosphate, and magnesium silicate.

The solutions charged to the compartments which contain or where a hydroxylammonium salt and/or hydroxylamine are produced may also optionally contain a stabilizer. In some instances, a stabilizer inhibits the decomposition of hydroxylammonium salt and/or hydroxylamine. Examples of stabilizers include quinoline derivatives, thiocarboxylic acids, thiosulfates, hydroxy anthraquinone, etc. Specific examples include 8-hydroxyquinoline, morin hydrate and quercetin. The amount of stabilizer in the solution may range from about $5\times10^{-4}\%$ to about 1% by weight based on the weight of electrolytes present.

In another embodiment, the solutions charged to the compartments which contain or where a hydroxylammonium salt and/or hydroxylamine are produced may also optionally contain a hydrogen suppressor. Hydrogen suppressors include thio compounds such as thiourea, and quaternary ammonium salts such as quaternary alkyl ammonium chlorides, nitrates, sulfates, bromides, phosphates, carbonates and bicarbonates. Specific quaternary alkyl ammonium ions include quaternary methyl ammonium, quaternary ethyl ammonium, quaternary propyl ammonium, quaternary butyl ammonium, dimethyidiethyl ammonium, methyltriethyl ammonium, and so on. In one embodiment, the amount of hydrogen suppressor in the solution may range from about 0.001% to about 10% by weight of the solution. In another embodiment, the amount of hydrogen suppressor in the solution may range from about 0.01% to about 1% by weight of the solution.

The hydroxylammonium salts which can be produced in the electrochemical cells from nitrogen containing compounds in accordance with the process of the present invention may be represented by the formula

$$(NR_2HOH)^+{}_yX^{-y}$$

wherein each R is independently hydrogen or a hydrocarbon group containing from 1 to about 8 carbon atoms, preferably 1 to about 6 carbon atoms, X is an anion of an acid, such as any of the acids described above, and y is a number equal to the valence of X. Specific examples of anions include Cl, Br $SO_4^{-2}$, $HSO_4^-$, $NO_3^-$, $PO_4^{-3}$, $H_2PO_4^{-1}$, $HPO_4^{-2}$, etc.

Specific examples of hydroxylammonium salts which can be prepared in accordance with this invention include hydroxylammonium sulfate, hydroxylammonium nitrate, hydroxylammonium chloride, hydroxylammonium bromide, hydroxylammonium fluoride, hydroxylammonium formate, hydroxylammonium acetate, hydroxylammonium phosphate, hydroxylammonium methylsulfonate, hydroxylammonium toluene sulfonate, methylhydroxylammonium nitrate, ethylhydroxylammonium nitrate, propylhydroxylammonium nitrate, isopropylhydroxylammonium nitrate, and diethylhydroxylammonium nitrate, phenylhydroxylammonium nitrate, etc.

The electrochemical cells used in the methods of the present invention can assume a number of different configurations. In one embodiment, the electrochemical cell contains at least two compartments including an anode, a cathode, and a divider (see FIGS. 2 and 5). In another embodiment, the electrochemical cell contains at least three compartments including an anode, a cathode, a bipolar membrane and a divider (see FIGS. 1, 3 and 4).

Figure 2:
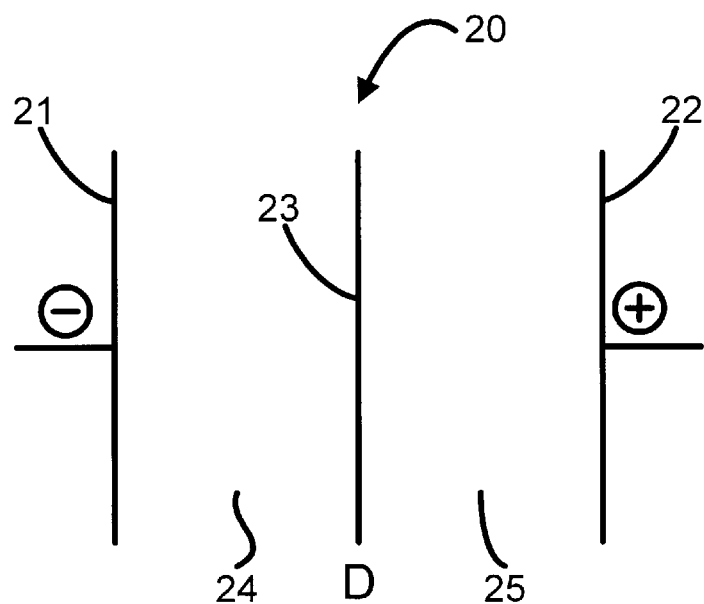
FIG. 2 is a schematic cross-section of an electrochemical cell useful in preparing hydroxylammonium salts according to the invention.

In one particular embodiment where hydroxylammonium salts are produced (starting with a solution containing a nitrogen containing compound and a mediator or an electrode having a mediator formed film thereon), the electrochemical cell contains an anode, a cathode, and a divider (see FIG. 2). In this embodiment, the divider is preferably a cation selective membrane. In some embodiments, additional dividers may be used in the cell, but they are not generally required.

Figure 3:
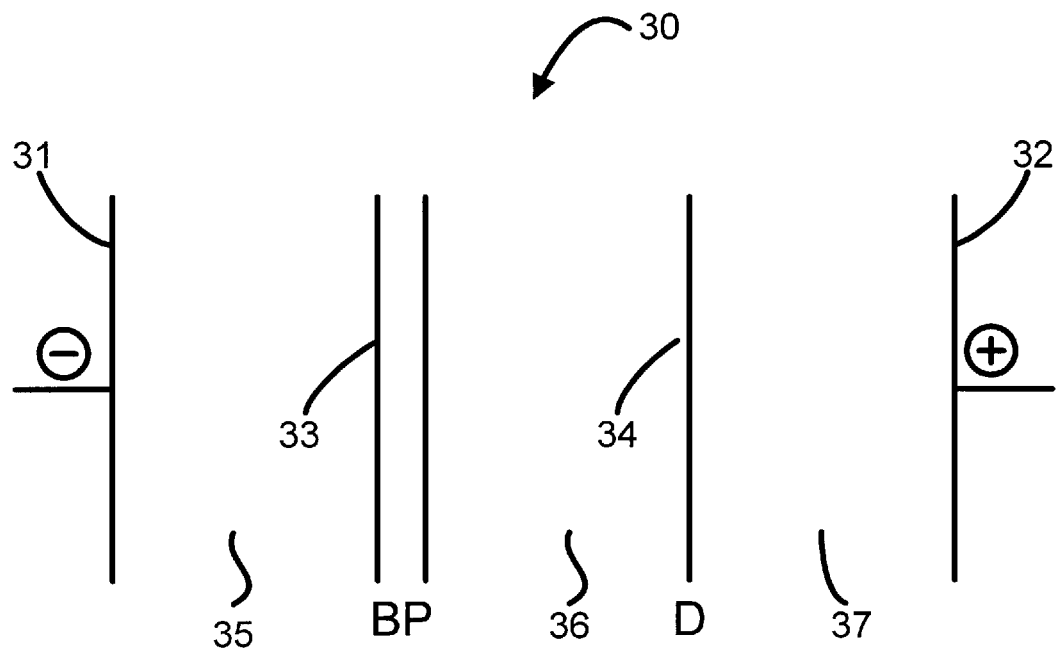
FIG. 3 is a schematic cross-section of an electrochemical cell useful in preparing hydroxylamine according to the invention.

In one particular embodiment where hydroxylamine is produced (starting with a solution containing a hydroxylammonium salt and a mediator or an electrode having a mediator formed film thereon), the electrochemical cell contains an anode, a cathode, a bipolar membrane, and a divider (see FIG. 3). In this embodiment, the divider is preferably an anion selective membrane. In some embodiments, additional dividers may be used in the cell, but they are not generally required.

Figure 4:
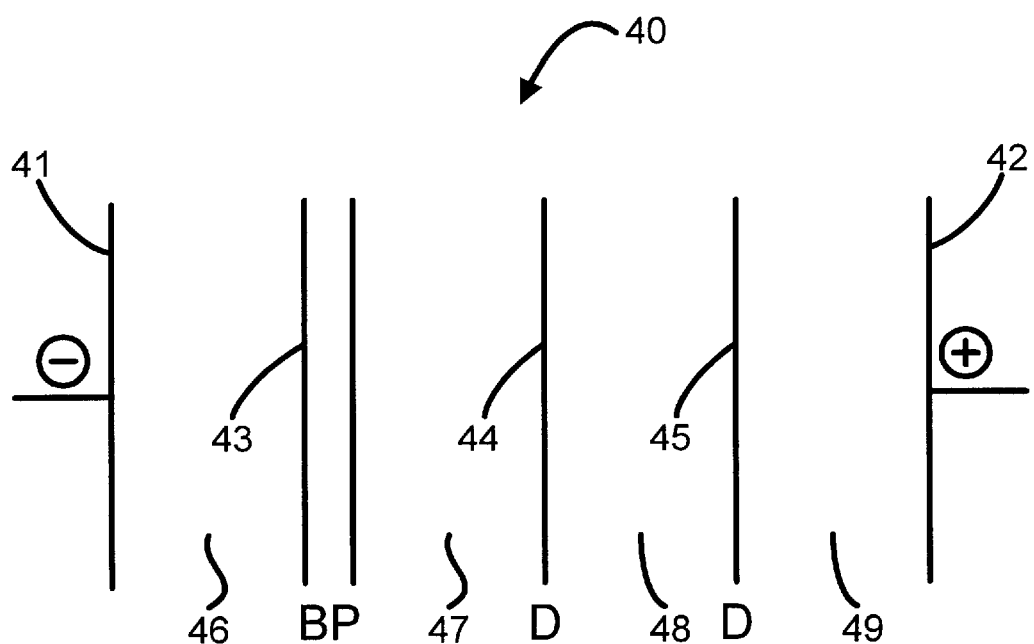
FIG. 4 is a schematic cross-section of an electrochemical cell useful in preparing hydroxylamine according to the invention.

For instance, in another particular embodiment where hydroxylamine is produced (starting with a solution containing a hydroxylammonium salt and a mediator or an electrode having a catalytic film thereon), the electrochemical cell contains an anode, a cathode, a bipolar membrane, and two dividers (see FIG. 4). In this embodiment, the two dividers include an anion selective membrane next to the anode and a cation selective membrane next to the bipolar membrane.

Figure 5:
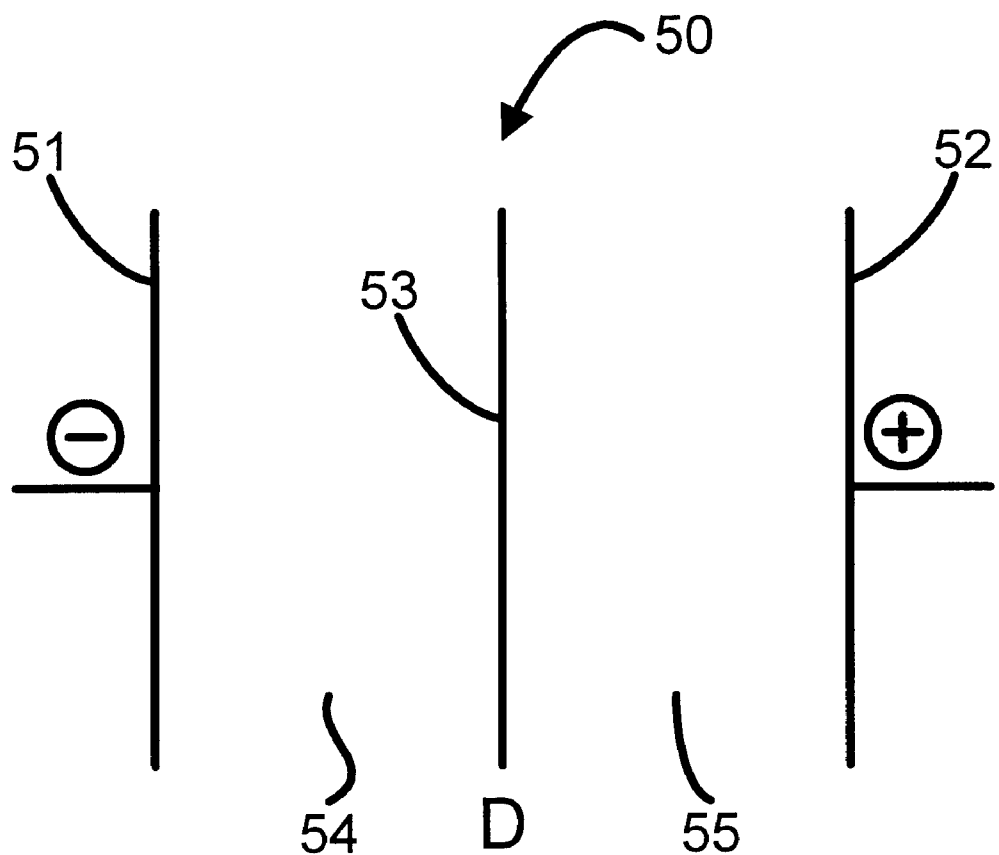
FIG. 5 is a schematic cross-section of an electrochemical cell useful in preparing hydroxylamine according to the invention.

In one particular embodiment where hydroxylamine is produced (starting with a solution containing a hydroxylammonium salt and a mediator or an electrode having a mediator formed film thereon), the electrochemical cell contains an anode, a cathode and a divider (see FIG. 5). In this embodiment, the divider is preferably an anion selective membrane and the cathode is preferably a gas diffusion cathode.

In a particular embodiment where both a hydroxylammonium salt and hydroxylamine are produced in a single cell, the electrochemical cell contains an anode, a cathode, a bipolar membrane and a divider (see FIG. 1). In this embodiment, the divider is preferably an anion selective membrane.

Accordingly, methods of making hydroxylammonium salts from a nitrogen containing compound involve the use of one electrochemical cell, while methods of making hydroxylamine from a nitrogen containing compound via a hydroxylammonium salt involve the use of one or at least two electrochemical cells. In embodiments where two electrochemical cells are used to make hydroxylamine, a hydroxylammonium salt is made in a first electrochemical cell (such as the cell in FIG. 2) and hydroxylamine is made in a second electrochemical cell (such as the cell in FIGS. 3, 4 or 5).

General speaking, the cells may be composed of cell materials which are compatible with the materials being charged into the cells. The cell materials must be particularly able to tolerate an acidic environment and sometimes a basic environment.

The cells may be adapted to operate at atmospheric pressure or at elevated pressures. In one embodiment the cell is one capable of operating at elevated pressures of at least about 1 psig up to about 10 psig or higher. Since the anode and cathode do not directly enter into the reaction, they also may be made from a variety of materials that do not react with the solutions added to the cells.

Suitable cathodes may comprise carbon such as graphite, stainless steel, glassy carbon, titanium, titanium oxide ceramic, niobium, tungsten carbide, silver, lead, chromium, zinc, mercury, manganese dioxide or platinum. For example, the cathode may comprise tungsten carbide, platinum on carbon, silver on carbon, manganese dioxide on carbon, or a platinized titanium. Graphite or carbon felt may be used with the cathode to increase the active surface area of the cathode. Cathodes under the trade designation Ebonex® may also be used.

In embodiments where the nitrogen containing compound is a nitrogen containing gas or hydroxylamine is produced in a two compartment electrochemical cell, the cathode is a gas diffusion cathode. The gas-diffusion cathode may comprise a conventional cathode structure formed of a suitable porous hydrophobic material such as polytetrafluoroethylene (PTFE), mixed with carbon black and a catalyst. In one preferred embodiment, the gas diffusion cathode is a hydrophobic cathode comprising a porous element having a surface portion which is in contact with a nitrogen containing gas charged to the catholyte compartment. For example, the gas diffusion cathode may comprise a porous material such as a PTFE fabric or a carbon cloth fabric coated on one side with a suitable catalytic material such as platinum, silver, gold, carbon, cobalt and mixtures thereof to form an "active layer." Specific preferable combinations include carbon-platinum, gold-platinum, silver-platinum and cobalt-platinum. Commercially available gas diffusion cathodes include an ELAT type gas diffusion cathode having an integrated stainless steel mesh current collector with an alloy of PtCo on a hydrophobic PTFE containing Vulcan XC-72 carbon and an EFCG type gas diffusion cathode having an integrated stainless steel mesh current collector with an alloy of PtCo on a Toray carbon substrate. In these embodiments, the electrochemical cell contains a gas chamber next to the gas diffusion cathode. A nitrogen containing gas is injected into the gas chamber and then forced through the gas diffusion cathode into the catholyte compartment. Such methods are described in U.S. Pat. No. 5,447,610 and U.S. patent application Ser. No. 08/734,858, both of which are hereby incorporated by reference. Also in this embodiment, the cathode may contain a material which exhibits electrocatalytic activity for nitrogen oxide reduction to hydroxylamine or hydroxylammonium salts.

Various materials can be used as anodes in the electrochemical cells. For example, the anode may be made of metals such as coated titanium electrodes, tantalum, zirconium, hafnium or alloys of the same. Generally, the anodes will have a non-passivable and catalytic film which may comprise metallic noble metals such as platinum, iridium, rhodium, ruthenium or alloys thereof, or a mixture of electroconductive oxides containing at least one oxide or mixed oxides of a noble metal such as platinum, iridium, ruthenium, palladium or rhodium. In one embodiment, the anode is a dimensionally stable anode such as an anode having a titanium base with ruthenium and/or iridium oxides thereon.

The electrochemical cell utilized in the process of most of the embodiments of the present invention contains at least one divider or separator, such as ionic or nonionic selective membranes. The dividers and/or bipolar membranes function as diffusion barriers and/or gas separators.

In one embodiment, the dividers or separators which can be utilized in the present invention can be selected from a wide variety of microporous diffusion barriers, screens, filters, diaphragms, etc., which contain pores of the desired size allow anions and/or cations of the hydroxylammonium salt to migrate toward one of the electrodes. The microporous dividers can be prepared from various materials including plastics such as polyethylene, polypropylene and Teflon, ceramics, etc. Microporous dividers such as nonionic dividers can be used, for example, in addition to the dividers listed in the Figures. Specific examples of commercially available microporous separators include: Celanese Celgard and Norton Zitex.

In one embodiment, the divider is an anion selective membrane. Any anion selective membrane may be utilized including membranes used in processes for the desalination of brackish water. Preferably, anion selective membranes should be selective with respect to the particular anions present in the cell (e.g., nitrate and halide ions). The preparation and structure of anionic membranes are described in the chapter entitled "Membrane Technology" in *Encyclopedia of Chemical Technology*, Kirk-Othmer, Third Ed., Vol. 15, pp. 92–131, Wiley & Sons, New York, 1985. These pages are hereby incorporated by reference for their disclosure of various anionic membranes which may be useful in the process of the present invention.

Among the anion selective membranes which may be utilized and which are commercially available are the following: AMFLON, Series 310, based on fluorinated polymer substituted with quaternary ammonium groups produced by American Machine and Foundry Company; IONAC MA 3148, MA 3236 and MA 3475, based on polymer substituted with quaternary ammonium derived from heterogenous polyvinylchloride produced by Ritter-Pfaulder Corp., Permutit Division; Tosflex IE-SF 34 or IE-SA 48 made by Tosoh Corp. which is a membrane designed to be stable in alkaline media; NEOSEPTA AMH, NEOSEPTA ACM, NEOSEPTA AFN or NEOSEPTA ACLE-SP from Tokuyama Soda Co.; and Selemion AMV and Selemion AAV from Asahi Glass.

In one embodiment, the divider is a cation selective membrane. The cation selective membranes used in the cells and the process of the invention may be any of those which have been used in the electrochemical purification or recycling of chemical compounds. Preferably, the cation-exchange membranes should contain a highly durable material such as the membranes based on the fluorocarbon series, or from less expensive materials of the polystyrene or polypropylene series. Preferably, however, the cation selective membranes useful in the present invention include fluorinated membranes containing cation selective groups such as perfluorosulfonic acid and perfluorosulfonic and/ perfluorocarboxylic acid, perfluorocarbon polymer membranes such as sold by the E.I. dupont Nemours & Co. under the general trade designation "Nafion" such as DuPont's Cationic Nafion 423 and 902 membrane. Other suitable cation selective membranes include styrenedivinyl benzene copolymer membranes containing cation selective groups such as sulfonate groups, carboxylate groups, etc. Raipore Cationic R1010, (from Pall RAI), and NEOSEPTA CMH and NEOSEPTA CM1 membranes from Tokuyama Soda are useful particularly with the higher molecular quaternary compounds. The preparation and structure of cation selective membranes are described in the chapter entitled "Membrane Technology" in *Encyclopedia of Chemical Technology*, Kirk-Othmer, Third Ed., Vol. 15, pp. 92–131, Wiley & Sons, New York, 1985. These pages are hereby incorporated by reference for their disclosure of various cation selective membranes which can be useful in the process of the present invention.

The bipolar membranes used in the electrochemical cells are composite membranes containing three parts: a cation selective side or region, an anion selective side or region, and an interface between the two regions. When a direct current passes across a bipolar membrane, with the cation selective side toward or facing the cathode, electrical conduction is achieved by the transport of $H^+$ and $OH^-$ ions which are produced by the dissociation of water which occurs at the interface under the influence of an electrical field. Bipolar membranes are described, for example, in U.S. Pat. Nos. 2,829,095, 4,024,043 (single film bipolar membranes) and in 4,116,889 (cast bipolar membranes). The bipolar membranes useful in the process of the present invention include NEOSEPTA BIPOLAR 1 by Tokuyama Soda, WSI BIPOLAR, and Aqualytics Bipolar membranes.

The anolyte compartment of the electrochemical cells (generally next to the anode) contains a solution of an ionic compound (an electrolyte solution). Aqueous solutions are preferred. The ionic compound in the anolyte compartment may be the same or different from the ionic compound in other compartments. Any suitable ionic compound can be used in the anolyte compartment, but in a preferred embodiment, the ionic compound in the anolyte compartment is an acid. The concentration of the ionic compound in the anolyte compartment is from about 0.1 M to about 10 M, and preferably from about 2 M to about 6 M. The concentration of the ionic compound in the anolyte compartment may be the same, higher or lower than the concentration of the ionic compound in the other compartments.

The catholyte compartment of the electrochemical cells (generally next to the cathode) contains different components depending upon which basic cell configuration is used or based upon whether one or more of hydroxylammonium salts and hydroxylamine are intended to be produced in a given electrochemical cell. For example, in embodiments where only hydroxylammonium salts are produced, hydroxylammonium salts and hydroxylamine are produced, or cells the same as or analogous to the electrochemical cells of FIGS. 1 and 2 are used, the catholyte compartment contains a solution of a nitrogen containing compound and a mediator and optionally an acid. In embodiments where the cathode of the electrochemical cell has a mediator formed film thereon, the catholyte compartment contains a solution of a nitrogen containing compound and optionally an acid (the mediator may be omitted because of the film). The choice of acid is determined by the particular hydroxylammonium salt desired to be produced. The acid may contain the anion of the desired hydroxylammonium salt. The concentration of nitrogen containing compound may be from about 0.01 M to about 10 M. Preferably the nitrogen containing compound concentration is from about 0.5 M to about 1 M. The concentration of the mediator, when present, may be from about 1 mM to about 1 M. Preferably the mediator concentration, when present, is from about 10 mM to about 100 mM. The concentration of acid may be from about 0.01 M to about 5 M. Preferably the acid concentration is from about 0.5 M to about 1 M.

In embodiments where only hydroxylamine is intended to be produced or cells the same as or analogous to the electrochemical cells of FIGS. 3 or 4 are used, the catholyte compartment contains a solution of an ionic compound (an electrolyte solution). Any ionic compound can be used in the catholyte compartment, but in a preferred embodiment, the ionic compound in the catholyte compartment is a base. In these embodiments, the concentration of the ionic compound in the catholyte compartment is from about 0.01 M to about 10 M, and preferably from about 0.1 M to about 1 M. The concentration of the ionic compound in the catholyte compartment may be the same, higher or lower than the concentration of the ionic compound in the other compartments, where present.

In embodiments where only hydroxylamine is intended to be produced or cells the same as or analogous to the electrochemical cell of FIG. 5 is used, the catholyte compartment contains a solution of a hydroxylammonium salt and a mediator. In other embodiments where only hydroxylamine is intended to be produced or cells the same as or analogous to the electrochemical cell of FIG. 5 is used and the cathode of the electrochemical cell has a mediator formed film thereon, the catholyte compartment contains a solution of a hydroxylammonium salt. The concentration of hydroxylammonium salt may be from about 0.1 M to about 10 M. Preferably the hydroxylammonium salt concentration is from about 0.5 M to about 2 M. The concentration of the mediator, when present, may be from about 1 mM to about 1 M. Preferably the mediator concentration, when present, is from about 10 mM to about 100 mM.

The recovery compartment of the electrochemical cell (generally a middle compartment and/or next to a bipolar membrane) initially contains a solution optionally containing an ionic compound. The ionic compound in the recovery compartment may be the same or different from the ionic compounds in the other compartments, where present. The concentration of the ionic compound in the recovery compartment is from about 0.01 M to about 10 M, and preferably from about 0.1 M to about 0.5 M. The concentration of the ionic compound in the recovery compartment may be the same, higher or lower than the concentration of the ionic compound in the other compartments. In some embodiments (see FIG. 3 for instance), the recovery compartment is charged with a solution of a hydroxylammonium salt and a mediator (when there is no mediator fromed film on the cathode). The concentration of hydroxylammonium salt may be from about 0.1 M to about 10 M. Preferably the hydroxylammonium salt concentration is from about 0.5 M to about 2 M. The concentration of the mediator, when present, may be from about 1 mM to about 1 M. Preferably the mediator concentration, when present, is from about 10 mM to about 100 mM. In the embodiment of FIG. 4, the feed compartment (generally a middle compartment) is charged with a solution of a hydroxylammonium salt and a mediator (same concentrations as above), when present, and the recovery compartment contains a solution with an optional ionic compound.

In embodiments where hydroxylammonium salt is produced in the catholyte compartment, hydroxylamine is produced in the catholyte compartment and/or hydroxylamine is produced in the recovery compartment, a current is applied between the anode and cathode with an apparent current density of about 0.1 ASI (amps per square inch) to about 10 ASI, more often from about 2 ASI to 4 ASI at about 3 volts to about 4 volts. The current is applied to the electrochemical cell for a period of time effective to produce the hydroxylammonium salt in the catholyte compartment, hydroxylamine is produced in the catholyte compartment and/or hydroxylamine in the recovery compartment at a desired concentration.

In embodiments where only hydroxylamine is produced in the recovery compartment, a current is applied between the anode and cathode with an apparent current density of about 0.1 ASI to about 2 ASI, more often from about 0.5 ASI to 1 ASI at about 2 volts to about 12 volts and about 3 to about 8 volts, respectively. The current is applied to the electrochemical cell for a period of time effective to produce the hydroxylamine in the recovery compartment at a desired concentration.

The electrochemical cell may be maintained at a temperature suitable for the production of hydroxylammonium salt and/or hydroxylamine.

The temperature is from about −20° C. to about 70° C., and preferably from about 1° C. to about 30° C.

The concentration of the hydroxylammonium salt produced in the catholyte compartment is from about 0.1 M to about 10 M, and preferably from about 0.5 M to about 2 M. A portion of the hydroxylammonium salt produced in the catholyte compartment is then either recovered or physically transferred to another electrochemical cell or a recovery compartment of the same cell (see, for example, FIG. 1). This may be accomplished on an intermittent or continuous basis by methods known to those skilled in the art. The concentration of hydroxylamine produced in the recovery compartment is from about 0.1 M to about 16 M, and preferably from about 2 M to about 5 M.

The electrochemical cells can be operated batchwise or in a continuous operation. Circulation is effected by pumping and/or by gas evolution. In one embodiment, the concentration of ionic compound in the catholyte, anolyte and/or recovery compartments is maintained at a substantially constant concentrations by the monitoring and employment of feeds into the compartments, such as a water feed into the anolyte compartment. Nitrogen containing compound and mediator can be added periodically or continuously to the catholyte compartment to maintain appropriate concentrations.

The solution obtained from the recovery compartment or catholyte compartment containing hydroxylamine can be further purified using at least one of distillation, reverse osmosis membrane technology, ion exchange and electrodialysis. Ion exchange techniques, using cation exchange resins and anion exchange resins, are known to those skilled in the art. Distillation techniques are known by those skilled in the art. For example, the hydroxylamine solution obtained from the recovery compartment can be further purified using vacuum distillation.

Reverse osmosis membranes are available from Fluid Systems, Filmtech, Osmonics, Inc., Desalination Systems Inc., and others. Specific examples include Fluid Systems TFCL-HP thin film composite membrane. Reverse osmosis membrane technology is known by those skilled in the art. For example, the hydroxylamine solution obtained from the recovery compartment containing hydroxylammonium salts is sent through a reverse osmosis membrane (for instance, polyamide based membrane) under high pressure (over 100 and often over 500 psi). Hydroxylamine passes through the membrane whereas the hydroxylammonium salts do not. Reverse osmosis membranes generally permit water and small molecular weight organics (such as hydroxylamine) to pass through while not permitting ionic compounds to pass.

The hydroxylamine solution obtained from the recovery compartment or the catholyte compartment can be further purified using electrodialysis in an electrodialytic cell. Electrodialytic techniques are known by those skilled in the art. For example, an electrodialytic cell can be provided containing, beginning at the cathode, a cathode, a bipolar membrane, an anion selective membrane (and optionally another bipolar membrane and another anion selective membrane), and an anode thereby defining, beginning again at the cathode, a water compartment, a feed-recovery compartment (and optionally a second acid compartment, and a second feed-recovery compartment), and an acid compartment. Water is charged to the water compartment, a hydroxylamine solution to be purified is charged to the feed-recovery compartment, and an acid solution is charged to the acid compartment. A current is applied and undesirable impurities migrate from the feed-recovery compartment to the acid compartment. A purified hydroxylamine solution is recovered from the feed-recovery compartment.

These additional procedures are effective for removing the mediator and/or impurities that may be present in the solution obtained from the recovery compartment or the catholyte compartment. The impurities include undesirable salts, ammonium ions, metals and organic materials. These additional procedures may also be used to for removing the mediator and/or impurities that may be present in the solutions containing a hydroxylammonium salt obtained from the catholyte compartment.

Examples of electrochemical cells useful in the processes of the present invention are discussed below and shown in FIGS. 1 to 5. Although the following discussion in connection with FIGS. 1 to 5 describes charging a mediator to the electrochemical cells, it will be understood that charging a mediator to the electrochemical cells is not necessary in instances where the cathode has a mediator formed film thereon.

Referring to FIG. 1, the electrochemical cell 10 is made of a cathode 11, an anode 12, and in sequence beginning at the cathode 11, a bipolar membrane 13 and a divider 14. In a preferred embodiment, the divider 14 is an anion selective membrane. The bipolar membrane 13 has an anion selective side (not shown) facing the anode and a cation selective side (not shown) facing the cathode. The electrochemical cell 10 contains three compartments; namely, a catholyte compartment 15, a recovery compartment 16, and an anolyte compartment 17.

In operation of the electrochemical cell illustrated in FIG. 1, a solution containing a nitrogen containing compound and a mediator is charged to the catholyte compartment 15. An electrolyte solution containing an ionic compound is charged to the recovery compartment 16 and the anolyte compartment 17. The ionic compound is at a first concentration in the recovery compartment and at a second concentration in the anolyte compartment 17. An electrical potential is established and maintained between the anode and the cathode to produce a flow of current across the electrochemical cell whereupon a hydroxylammonium salt is produced in the catholyte compartment 15. A portion of the catholyte solution containing the hydroxylammonium salt is either collected or physically removed from the catholyte compartment 15 as shown by line 18 and transferred to the recovery compartment 16. As a result of the electrical potential maintained between the anode and the cathode, the salt (anion) of the hydroxylammonium salt is attracted towards the anode 12 thereby passing through the divider 14 into the anolyte compartment 17. Hydroxylamine is produced in the recovery compartment 16. Hydroxylamine is then recovered from the recovery compartment 16. The hydroxylamine and/or hydroxylammonium salt (before it is charged to the recovery compartment) may be purified by further treatment using one or more of distillation, reverse osmosis, electrodialysis and ion exchange techniques.

In a preferred embodiment, a portion of the solution in the anolyte compartment may be physically removed and transferred, as shown by line 19, to the catholyte compartment 15. In an even more preferred embodiment, the acid solution obtained from the anolyte compartment is concentrated before it is added to the catholyte compartment. As the salt anion from the hydroxylammonium salt migrates through the divider 14 into the anolyte compartment 17, an acid corresponding to the salt is produced in the anolyte compartment.

As needed, various compounds such as one or more acids, water, one or more ionic compounds, nitrogen containing compounds, mediators, stabilizers and the like may be added or recovered from the catholyte, recovery and anolyte compartments in order to maintain efficient operation of the electrochemical cell. For example, nitrogen containing compound must be continuously or intermittently added to the catholyte compartment. From time to time, it may also be necessary to intermittently or continuously remove acid from the anolyte compartment.

Although the embodiment described in FIG. 1 illustrates the formation of a generic hydroxylammonium salt, the electrochemical cells and the method described can be utilized to prepare many desired specific hydroxylammonium salts by utilizing the different acids described above. Thus, a hydroxylammonium chloride salt can be prepared utilizing hydrochloric acid solutions, a hydroxylammonium sulfate salt can be prepared utilizing sulfuric acid solutions, a hydroxylammonium nitrate salt can be prepared utilizing nitric acid solutions, hydroxylammonium borate salts can be prepared utilizing boric acid, and formate or acetate salts can be prepared by utilizing formic acid or acetic acid.

Referring to FIG. 2, the electrochemical cell 20 is made of a cathode 21, an anode 22, and a divider 23. In a preferred embodiment, the divider 23 is a cation selective membrane. The electrochemical cell 20 contains two compartments; namely, a catholyte compartment 24 and an anolyte compartment 25.

In operation of the electrochemical cell illustrated in FIG. 2, a solution containing a nitrogen containing compound and a mediator is charged to the catholyte compartment 24. An electrolyte solution containing an ionic compound is charged to the anolyte compartment 25. In a preferred embodiment, the ionic compound is an acid. An electrical potential is established and maintained between the anode and the cathode to produce a flow of current across the electrochemical cell whereupon a hydroxylammonium salt is produced in the catholyte compartment 24. A hydroxylammonium salt is recovered from the catholyte compartment 24. The hydroxylammonium salt may be purified by further treatment using one or more of distillation, reverse osmosis, electrodialysis and ion exchange techniques.

Referring to FIG. 3, the electrochemical cell 30 is made of a cathode 31, an anode 32, and in sequence beginning at the cathode 31, a bipolar membrane 33 and a divider 34. In a preferred embodiment, the divider 34 is an anion selective membrane. The bipolar membrane 33 has an anion selective side (not shown) facing the anode and a cation selective side (not shown) facing the cathode. The electrochemical cell 30 contains three compartments; namely, a catholyte compartment 35, a recovery compartment 36, and an anolyte compartment 37.

In operation of the electrochemical cell illustrated in FIG. 3, a solution containing a hydroxylammonium salt and a mediator is charged to the recovery compartment 36. A solution containing an ionic compound is charged to the catholyte compartment 35 and the anolyte compartment 37. The ionic compound of the catholyte compartment is the same or different than the ionic compound in the anolyte compartment. In a preferred embodiment, the ionic compound in the catholyte compartment is a base while the ionic compound in the anolyte compartment is an acid. An electrical potential is established and maintained between the anode and the cathode to produce a flow of current across the electrochemical cell whereupon hydroxylamine is produced in the recovery compartment 36. As a result of the electrical potential maintained between the anode and the cathode, the salt (anion) of the hydroxylammonium salt is attracted towards the anode 32 thereby passing through the divider 34 into the anolyte compartment 37. Hydroxylamine is then recovered from the recovery compartment 36. The hydroxylamine may be purified by further treatment using one or more distillation, reverse osmosis, electrodialysis and ion exchange techniques.

Referring to FIG. 4, the electrochemical cell 40 is made of a cathode 41, an anode 42, and in sequence beginning at the cathode 41, a bipolar membrane 43, a first divider 44 and a second divider 45. In a preferred embodiment, the first divider 44 is a cation selective membrane and the second divider 45 is an anion selective membrane. The bipolar membrane 43 has an anion selective side (not shown) facing the anode and a cation selective side (not shown) facing the cathode. The electrochemical cell 40 contains four compartments; namely, a catholyte compartment 46, a recovery compartment 47, a feed compartment 48, and an anolyte compartment 49.

In operation of the electrochemical cell illustrated in FIG. 4, a solution containing a hydroxylammonium salt and a mediator is charged to the feed compartment 48. A solution containing an ionic compound is charged to the catholyte compartment 35 and the anolyte compartment 37. A solution optionally containing an ionic compound is charged to the recovery compartment 47. The ionic compound of the catholyte compartment is the same or different than the ionic compound in the anolyte compartment (and/or recovery compartment). In a preferred embodiment, the ionic compound in the catholyte compartment is a base while the ionic compound in the anolyte compartment is an acid. An electrical potential is established and maintained between the anode and the cathode to produce a flow of current across the electrochemical cell whereupon hydroxylamine is produced in the recovery compartment 47. As a result of the electrical potential maintained between the anode and the cathode, the salt (anion) of the hydroxylammonium salt is attracted towards the anode 42 thereby passing through the second divider 45 into the anolyte compartment 49. Hydroxylamine is then recovered from the recovery compartment 47. The hydroxylamine may be purified by further treatment using one or more of distillation, reverse osmosis, electrodialysis and ion exchange techniques.

Referring to FIG. 5, the electrochemical cell 50 is made of a cathode 51, an anode 52, and a divider 53. In a preferred embodiment, the divider 53 is an anion selective membrane and the cathode is a gas diffusion cathode. The electrochemical cell 50 contains two compartments; namely, a catholyte compartment 54 and an anolyte compartment 55.

In operation of the electrochemical cell illustrated in FIG. 5, a solution containing a hydroxylammonium salt and a mediator is charged to the catholyte compartment 54. A solution containing an ionic compound is charged to the anolyte compartment 55. In a preferred embodiment, the ionic compound in the anolyte compartment is an acid. An electrical potential is established and maintained between the anode and the cathode to produce a flow of current across the electrochemical cell whereupon hydroxylamine is produced in the catholyte compartment 54. As a result of the electrical potential maintained between the anode and the cathode, the salt (anion) of the hydroxylammonium salt is attracted towards the anode 52 thereby passing through the divider 53 into the anolyte compartment 55. Hydroxylamine is then recovered from the catholyte compartment 54. The hydroxylamine may be purified by further treatment using one or more distillation, reverse osmosis, electrodialysis and ion exchange techniques.

The following specific examples further illustrate the preparation of the hydroxylammonium salts and hydroxylamine according to the present invention. Unless otherwise indicated in the examples and elsewhere in the specification and claims, all parts and percentages are by weight, temperatures are in degrees centigrade, and pressures are at or near atmospheric pressure.

EXAMPLE 1

An electrochemical cell according to FIG. 2 is provided containing an anode made of ruthenium oxide coated titanium, a cathode made of graphite, and a Nafion 423 cation selective membrane as the divider. A solution containing 1 M nitric acid and 50 mM 1,4-phenylenediamine is charged to the catholyte compartment. A solution of 4 M nitric acid is charged to the anolyte compartment. Nitric acid is added to the catholyte compartment to maintain the nitric acid concentration between 0.5 M and 1 M under application of an electrical current. While maintaining the temperature between 5° C. and 10° C., a current of 5 Amps (0.3 ASI) and a cell voltage of about 3.5 volts is applied. The catholyte is stirred under application of the current. A solution of 1.3 M hydroxylammonium nitrate and 0.8 M nitric acid with no detectable ammonium nitrate is obtained from the catholyte compartment. An overall current efficiency of 60% for formation of hydroxylammonium nitrate is achieved.

EXAMPLE 2

An electrochemical cell according to FIG. 2 is provided containing an anode made of ruthenium oxide coated titanium, a cathode made of graphite, and a Nafion 423 cation selective membrane as the divider. Graphite felt is attached to the graphite cathode to enhance the active cathode surface area. A solution containing 1 M nitric acid and 50 mM 1,4-phenylenediamine is charged to the catholyte compartment. A solution of 4 M nitric acid is charged to the anolyte compartment. Nitric acid is added to the catholyte compartment to maintain the nitric acid concentration between 0.5 M and 1 M under application of an electrical current. While maintaining the temperature between 5° C. and 1° C., a current of 45 Amps (3 ASI) and a cell voltage of about 6.5 volts is applied. The catholyte is stirred under application of the current. A solution of 1.7 M hydroxylammonium nitrate and 0.6 M nitric acid with no detectable ammonium nitrate is obtained from the catholyte compartment. An overall current efficiency of 75% for formation of hydroxylammonium nitrate is achieved.

EXAMPLE 3

An electrochemical cell according to FIG. 3 is provided containing an anode made of ruthenium oxide coated titanium, a stainless steel cathode, a Tokuyama Bipolar 1 bipolar membrane, a Asahi glass AAV anion selective membrane as the divider. A solution of 0.5 M sodium hydroxide is charged to the catholyte compartment, a solution of 0.3 M nitric acid is charged to the anolyte compartment, and a solution of 1.7 M hydroxylamine nitrate, 0.7 M nitric acid and 50 mM of 1,4-phenylenediamine is charged to the recovery compartment. While maintaining the temperature between 5° C. and 10° C., a current of 5 Amps and a cell voltage of about 9.1 volts is applied. A solution containing 1.6 M hydroxylamine and 50 mM of 1,4-phenylenediamine is recovered from the recovery compartment. Pure hydroxylamine is obtained after purification by distillation.

EXAMPLE 4

An electrochemical cell according to FIG. 2 is provided containing an anode made of ruthenium oxide coated titanium, a cathode made of graphite, and a Nafion 423 cation selective membrane as the divider. Graphite felt is attached to the graphite cathode to enhance the active cathode surface area. A solution containing 1 M nitric acid and 50 mM to 100 mM anthraquinone-2,6-disulfonic acid disodium salt is charged to the catholyte compartment. A solution of 4 M nitric acid is charged to the anolyte compartment. Nitric acid is added to the catholyte compartment to maintain the nitric acid concentration between 0.5 M and 1 M under application of an electrical current. While maintaining the temperature between 5° C. and 10° C., a current of 15 Amps (1 ASI) and a cell voltage of about 3.5 volts is applied. The catholyte is stirred under application of the current. A solution of 1.1 M hydroxylammonium nitrate and 0.9 M nitric acid and 0.05 M ammonium nitrate is obtained from the catholyte compartment. An overall current efficiency of 35% for formation of hydroxylammonium nitrate is achieved.

EXAMPLE 5

An electrochemical cell according to FIG. 2 is provided containing an anode made of ruthenium oxide coated titanium, a cathode made of graphite, and a Nafion 423 cation selective membrane as the divider. Graphite felt is attached to the graphite cathode to enhance the active cathode surface area. A solution containing 1 M nitric acid and 50 mM to 400 mM 4-4'-oxydianiline is charged to the catholyte compartment. A solution of 4 M nitric acid is charged to the anolyte compartment. Nitric acid is added to the catholyte compartment to maintain the nitric acid concentration between 0.5 M and 1 M under application of an electrical current. While maintaining the temperature between 5° C. and 10° C., a current of 30 Amps (2 ASI) and a cell voltage of about 6 volts is applied. The catholyte is stirred under application of the current. A solution of 1.9 M hydroxylammonium nitrate and 0.8 M nitric acid with no detectable ammonium nitrate is obtained from the catholyte compartment. An overall current efficiency of 60% for formation of hydroxylammonium nitrate is achieved.

EXAMPLE 6

An electrochemical cell according to FIG. 2 is provided containing an anode made of ruthenium oxide coated titanium, a cathode made of graphite, and a Nafion 423 cation selective membrane as the divider. Carbon felt is attached to the graphite cathode to enhance the active cathode surface area. A solution containing 1 M nitric acid and 50 mM to 0.1 M tin chloride is charged to the catholyte compartment. A solution of 4 M nitric acid is charged to the anolyte compartment. Nitric acid is added to the catholyte compartment to maintain the nitric acid concentration between 0.5 M and 1 M under application of an electrical current. While maintaining the temperature between 5° C. and 10° C., a current of 15 Amps (1 ASI) and a cell voltage of about 4.5 volts is applied. The catholyte is stirred under application of the current. A solution of 1.2 M hydroxylammonium nitrate and 1.2 M nitric acid and 0.1 M ammonium nitrate is obtained from the catholyte compartment. An overall current efficiency of 40% for formation of hydroxylammonium nitrate is achieved.

EXAMPLE 7

An electrochemical cell according to FIG. 2 is provided containing an anode made of ruthenium oxide coated titanium, a cathode made of niobium, and a Nafion 423 cation selective membrane as the divider. A solution containing 1 M nitric acid and 50 mM 1,4-phenylenediamine is charged to the catholyte compartment. A solution of 4 M nitric acid is charged to the anolyte compartment. Nitric acid is added to the catholyte compartment to maintain the nitric acid concentration between 0.5 M and 1 M under application of an electrical current. While maintaining the temperature between 5° C. and 10° C., a current of 5 Amps (0.3 ASI) and a cell voltage of about 3 volts is applied. The catholyte is stirred under application of the current. A solution of 0.8 M hydroxylammonium nitrate and 0.9 M nitric acid and 0.03 M ammonium nitrate is obtained from the catholyte compartment. An overall current efficiency of 45% for formation of hydroxylammonium nitrate is achieved.

EXAMPLE 8

The general procedure of Example 1 is repeated except that a piece of graphite felt is attached to the graphite cathode to enhance the cathode surface area. A solution containing 0.5 M nitric acid and 50 mM 1,4-phenylenediamine is charged to the catholyte compartment. Concentrated nitric acid is added to the catholyte compartment to maintain the nitric acid concentration between 0.5 M and 1 M under application of an electrical current. While maintaining the temperature between 5° C. and 10° C., a current of 20 amps (5 ASI) and a cell voltage of about 5.5 volts is applied. The catholyte is stirred under application of the current. A solution of 1.67 M hydroxylammonium nitrate and 0.50 M nitric acid with no detectable ammonium nitrate is obtained from the catholyte compartment. An overall current efficiency of 85% for formation of hydroxylammonium nitrate is achieved.

EXAMPLE 9

Using the emptied cell from Example 8 (the cathode has a mediator formed film over its surface due, in part, to use of 1,4-phenylenediamine), the general procedure of Example 8 is repeated except that no 1,4-phenylenediamine is added to the catholyte solution. A solution containing 0.5 M nitric acid is charged to the catholyte compartment including the cathode electrode of Example 8. Concentrated nitric acid is added to the catholyte compartment to maintain the nitric acid concentration between 0.5 M and 1 M under application of an electrical current. While maintaining the temperature between 5° C. and 10° C., a current of 20 amps (5 ASI) and a cell voltage of about 6 volts is applied. The catholyte is stirred under application of the current. A solution of 1.35 M hydroxylammonium nitrate and 0.6 M nitric acid with no detectable ammonium nitrate is obtained from the catholyte compartment. An overall current efficiency of 70% for formation of hydroxylammonium nitrate is achieved.

EXAMPLE 10

The general procedure of Example 8 is repeated except that a solution containing 1.0 M nitric acid and 70 ppm p-aminophenol is charged to the catholyte compartment. A solution of 4 M nitric acid is charged to the anolyte compartment. Concentrated nitric acid is added to the catholyte compartment to maintain the nitric acid concentration between 0.5 M and 1 M under application of an electrical current. While maintaining the temperature between 5° C. and 10° C., a current of 20 amps (5 ASI) and a cell voltage of about 5 volts is applied. A solution of 1.26 M hydroxylammonium nitrate and 0.7 M nitric acid with no detectable ammonium nitrate is obtained from the catholyte compartment. An overall current efficiency of 74% for formation of hydroxylammonium nitrate is achieved.

EXAMPLE 11

The general procedure of Example 8 is repeated except that a solution of 1 M nitric acid and 100 ppm hydroquinone is charged to the catholyte compartment. A solution of 4 M nitric acid is charged to the anolyte compartment. Concentrated nitric acid is added to the catholyte compartment to maintain the nitric acid concentration between 0.5 M and 1 M under application of an electrical current. While maintaining the temperature between 5° C. and 10° C., a current of 20 amps (5 ASI) and a cell voltage of about 6.5 volts is applied. A solution of 1.3 M hydroxylammonium nitrate and 0.8 M nitric acid with no detectable ammonium nitrate is obtained from the catholyte compartment. An overall current efficiency of 60% for formation of hydroxylammonium nitrate is achieved.

EXAMPLE 12

Using the emptied cell from Example 8 (the cathode has a mediator formed film over its surface due, in part, to use of 1,4-phenylenediamine), the general procedure of Example 8 is repeated except that a solution of 1 M hydrochloric acid and 1 M nitrobenzene (instead of nitric acid) is charged and no 1,4-phenylenediamine is added to the catholyte compartment of a cell. A solution of 4 M nitric acid is charged to the anolyte compartment. While maintaining the temperature between 25° C. and 30° C., a current of 10 amps (2.5 ASI) and a cell voltage of about 5.5 volts is applied. The catholyte is stirred under application of the current. A solution of 0.9 M phenylhydroxylammonium chloride is obtained from the catholyte compartment. An overall current efficiency of 55% for formation of phenylhydroxylammonium chloride is achieved.

EXAMPLE 13

The general procedure of Example 8 is repeated except that thiourea is also added into the catholyte compartment. A solution of 1 M nitric acid, 50 mM 1,4-phenylenediamine and 250 mM of thiourea is charged to the catholyte compartment. A solution of 4 M nitric acid is charged to the anolyte compartment. Nitric acid is added to the catholyte compartment to maintain the nitric acid concentration between 0.5 M and 1 M under application of an electrical current. While maintaining the temperature between 5° C. and 10° C., a current of 45 amps (3 ASI) and a cell voltage of about 6.5 volts is applied. The catholyte is stirred under application of the current. A solution of 1.77 M hydroxylammonium nitrate and 0.5 M nitric acid with no detectable ammonium nitrate is obtained from the catholyte compartment. An overall current efficiency of 90% for formation of hydroxylammonium nitrate is achieved.

EXAMPLE 14

The general procedure of Example 8 is repeated except that tetrabutylammonium chloride is added into the catholyte compartment. A solution of 1 M nitric acid, 50 mM 1,4-phenylenediamine and 0.1 M tetrabutylammonium chloride is charged to the catholyte compartment. A solution of 4 M nitric acid is charged to the anolyte compartment. Nitric acid is added to the catholyte compartment to maintain the nitric acid concentration between 0.5 M and 1 M under application of an electrical current. While maintaining the temperature between 5° C. and 10° C., a current of 45 amps (3 ASI) and a cell voltage of about 6.5 volts is applied. The catholyte is stirred under application of the current. A solution of 1.65 M hydroxylammonium nitrate and 0.7 M nitric acid with no detectable ammonium nitrate is obtained from the catholyte compartment. An overall current efficiency of 85% for formation of hydroxylammonium nitrate is achieved.

EXAMPLE 15

Using the emptied cell from Example 8 (the cathode has a mediator formed film over its surface due, in part, to use of 1,4-phenylenediamine), the general procedure of Example 8 is repeated except that a solution 1 M nitrobenzene is also charged and no 1,4-phenylenediamine is added to the catholyte compartment of a cell. A solution of 4 M nitric acid is charged to the anolyte compartment. While maintaining the temperature between 25° C. and 30° C., a current of 10 amps (2.5 ASI) and a cell voltage of about 5.5 volts is applied. The catholyte is stirred under application of the current. A solution of 0.9 M phenylhydroxylammonium nitrate is obtained from the catholyte compartment. An overall current efficiency of 55% for formation of phenylhydroxylammonium nitrate is achieved.

The present invention provides efficient, inexpensive and uncomplicated electrochemical methods of preparing hydroxylammonium salts and hydroxylamine of high purity. Since the use of mercury containing and/or lead containing cathodes is not required, the present invention does not raise toxicity concerns and is environmentally friendly. Since in some embodiments the use of gas permeable cathodes is not required, the present invention is relatively inexpensive and uncomplicated to practice.

While the invention has been explained in relation to its preferred embodiments, it is to be understood that various modifications thereof will become apparent to those skilled in the art upon reading this specification. Therefore, it is to be understood that the invention disclosed herein is intended to cover such modifications as fall within the scope of the appended claims.

What is claimed is:

1. A method of preparing a hydroxylammonium salt, comprising the steps of:
   (A) providing an electrochemical cell comprising an anode, a cathode, and a divider positioned between the anode and the cathode, to define a catholyte compartment between the cathode and the divider and an anolyte compartment between the anode and the divider;
   (B) charging the catholyte compartment with a first solution comprising a nitrogen containing compound and a mediator and the anolyte compartment with a second solution comprising an ionic compound;
   (C) passing a current through the electrochemical cell to produce a hydroxylammonium salt in the catholyte compartment; and
   (D) recovering the hydroxylammonium salt from the catholyte compartment.

2. The method of claim 1, wherein the mediator comprises an organic mediator.

3. The method of claim 1, wherein the mediator comprises an inorganic mediator.

4. The method of claim 1, wherein the mediator comprises at least one of 1,4-phenylenediamine; 1,3-phenylenediamine; tetracyanoquinodimethane; N,N,N',N'-tetramethyl-p-phenylenediamine; p-aminophenol; m-aminophenol; o-aminophenol; aminothiophenols; tetrathiafulvalene; thianthrene; tri-N-p-tolyamine; ferrocene; methylviologen dichloride hydrate; hydroquinone; aminoanthraquinones; aminoanthraquinone-2-sulfonic acid sodium salt; anthraquinone-1,5-disulfonic acid disodium salt; anthraquinone-2,6-disulfonic acid disodium salt; acetanilide, 4-bromo-2,3,5,6-tetrafluoroaniline, 4,4'-oxydianiline; 4'-aminoacetanilide; 1,10-phenanthroline; phenazine; 1,8-diaminonaphthalene; 1,4-diacetylbenzene; terephthaldicarboxaldehyde; terephthalic acid; and 2,5-dichloro-1,4-phenylenediamine.

5. The method of claim 1, wherein the mediator comprises at least one of a cesium compound, a chromium compound, a cobalt compound, a copper compound, a manganese compound, a periodate compound, a silver compound, a sodium compound, a tin compound, a titanium compound, and a zinc compound.

6. The method of claim 1, wherein the hydroxylammonium salt comprises hydroxylammonium nitrate.

7. The method of claim 1, wherein the mediator forms a film on the cathode.

8. The method of claim 1, wherein the nitrogen containing compound comprises nitric acid.

9. In a method of making a hydroxylammonium salt by reducing a nitrogen containing compound, the improvement comprising using a mediator with the nitrogen containing compound.

10. The method of claim 9, wherein the mediator comprises at least one of an organic mediator and an inorganic mediator.

11. The method of claim 9, wherein the mediator is at least one of 1,4-phenylenediamine; 1,3-phenylenediamine; tetracyanoquinodimethane; N,N,N',N'-tetramethyl-p-phenylenediamine; p-aminophenol; m-aminophenol; o-aminophenol; aminothiophenols; tetrathiafulvalene; thianthrene; tri-N-p-tolyamine; ferrocene; methylviologen dichloride hydrate; hydroquinone; aminoanthraquinones; aminoanthraquinone-2-sulfonic acid sodium salt; anthraquinone-1,5-disulfonic acid disodium salt; anthraquinone-2,6-disulfonic acid disodium salt; acetanilide, 4-bromo-2,3,5,6-tetrafluoroaniline, 4,4'-oxydianiline; 4'-aminoacetanilide; 1,10-phenanthroline; phenazine; 1,8-diaminonaphthalene; 1,4-diacetylbenzene; terephthaldicarboxaldehyde; terephthalic acid; and 2,5-dichloro-1,4-phenylenediamine.

12. The method of claim 9, wherein the mediator is an amino-aromatic compound.

13. A method of preparing hydroxylamine, comprising the steps of:
   (A) providing an electrochemical cell comprising an anode, a cathode and a divider positioned between the cathode and the anode, to define a catholyte compartment between the divider and the cathode and an anolyte compartment between the divider and the anode;
   (B) charging the catholyte compartment with a solution comprising a hydroxylammonium salt and a mediator, and the anolyte compartment with a first electrolyte solution;
   (C) passing a current through the electrochemical cell to produce hydroxylamine in the catholyte compartment; and
   (D) recovering hydroxylamine from the catholyte compartment.

14. The method of claim 13, wherein the mediator comprises an organic mediator.

15. The method of claim 13, wherein the mediator comprises an inorganic mediator.

16. The method of claim 13, wherein the mediator comprises at least one of 1,4-phenylenediamine; 1,3-phenylenediamine; tetracyanoquinodimethane; N,N,N',N'- tetramethyl-p-phenylenediamine; p-aminophenol; m-aminophenol; o-aminophenol; aminothiophenols; tetrathiafulvalene; thianthrene; tri-N-p-tolyamine; ferrocene; methylviologen dichloride hydrate; hydroquinone; aminoanthraquinones; aminoanthraquinone-2-sulfonic acid sodium salt; anthraquinone-1,5-disulfonic acid disodium salt; anthraquinone-2,6-disulfonic acid disodium salt; acetanilide, 4-bromo-2,3,5,6-tetrafluoroaniline, 4,4'-oxydianiline; 4'-aminoacetanilide; 1,10-phenanthroline; phenazine; 1,8-diaminonaphthalene; 1,4-diacetylbenzene; terephthaldicarboxaldehyde; terephthalic acid; and 2,5-dichloro-1,4-phenylenediamine.

17. The method of claim 13, wherein the mediator comprises at least one of a cesium compound, a chromium compound, a cobalt compound, a copper compound, a manganese compound, a periodate compound, a silver compound, a sodium compound, a tin compound, a titanium compound, and a zinc compound.

18. The method of claim 13 further comprising the step of purifying the hydroxylamine recovered from the catholyte compartment by at least one of distillation and ion exchange.

19. The method of claim 13, wherein the divider is an anion selective membrane.

20. The method of claim 13, wherein the hydroxylammonium salt is obtained by:
(A) providing a preliminary electrochemical cell comprising an anode, a cathode and a divider positioned between the cathode and the anode, to define a catholyte compartment between the cathode and the divider and an anolyte compartment between the divider and the anode;
(B) charging the catholyte compartment with a first solution comprising a nitrogen containing compound and the mediator and the anolyte compartment with a second solution comprising an acid;
(C) passing a current through the preliminary electrochemical cell to produce the hydroxylammonium salt in the catholyte compartment; and
(D) transferring the hydroxylammonium salt from the catholyte compartment of the preliminary electrochemical cell to the catholyte compartment of the electrochemical cell.

21. The method of claim 13, wherein the electrochemical cell further comprises a bipolar membrane positioned between the divider and the cathode, the bipolar membrane having an anion selective side facing the anode and a cation selective side facing the cathode, to additionally define a recovery compartment between the divider and the bipolar membrane; the recovery compartment is charged with a solution comprising a hydroxylammonium salt and a mediator, and the catholyte compartment is charged with a second electrolyte solution; hydroxylamine is produced in the recovery compartment; and hydroxylamine is recovered from the recovery compartment.

22. The method of claim 21, wherein the divider is a first divider and the electrochemical cell further comprises a second divider between the bipolar membrane and the first divider to define a feed compartment between the first divider and the second divider and the recovery compartment between the second divider and the bipolar membrane; a solution comprising the hydroxylammonium salt and the mediator is charged to the feed compartment; and a third electrolyte solution is charged to the recovery compartment.

23. The method of claim 22, wherein the first divider is a anion selective membrane and the second divider is a cation selective membrane.

24. In a method of making a hydroxylamine from a hydroxylammonium salt in an electrochemical cell, the improvement comprising using a mediator with the hydroxylammonium salt.

25. The method of claim 24, wherein the mediator comprises at least one of an organic mediator and an inorganic mediator.

26. The method of claim 24, wherein the mediator comprises at least one of 1,4-phenylenediamine; 1,3-phenylenediamine; tetracyanoquinodimethane; N,N,N',N'-tetramethyl-p-phenylenediamine; p-aminophenol; m-aminophenol; o-aminophenol; aminothiophenols; tetrathiafulvalene; thianthrene; tri-N-p-tolyamine; ferrocene; methylviologen dichloride hydrate; hydroquinone; aminoanthraquinones; aminoanthraquinone-2-sulfonic acid sodium salt; anthraquinone-1,5-disulfonic acid disodium salt; anthraquinone-2,6-disulfonic acid disodium salt; acetanilide, 4-bromo-2,3,5,6-tetrafluoroaniline, 4,4'-oxydianiline; 4'-aminoacetanilide; 1,10-phenanthroline; phenazine; 1,8-diaminonaphthalene; 1,4-diacetylbenzene; terephthaldicarboxaldehyde; terephthalic acid; and 2,5-dichloro-1,4-phenylenediamine.

27. The method of claim 24, wherein the mediator comprises an amino-aromatic compound.

28. A method of preparing a hydroxylammonium salt, comprising the steps of:
(A) providing an electrochemical cell comprising an anode, a cathode, and a divider positioned between the anode and the cathode, to define a catholyte compartment between the cathode and the divider and an anolyte compartment between the anode and the divider, wherein the cathode has a film thereon formed from a mediator;
(B) charging the catholyte compartment with a first solution comprising a nitrogen containing compound and the anolyte compartment with a second solution comprising an ionic compound;
(C) passing a current through the electrochemical cell to produce a hydroxylammonium salt in the catholyte compartment; and
(D) recovering the hydroxylammonium salt from the catholyte compartment.

29. The method of claim 28, wherein the film has a thickness from about 0.1 nm to about 500 $\mu$m.

* * * * *